United States Patent [19]

Aid et al.

[11] Patent Number: 4,554,069
[45] Date of Patent: Nov. 19, 1985

[54] PRESSURE REGULATOR

[75] Inventors: James D. Aid, St. Petersburg; Edward R. Lindsay, Clearwater, both of Fla.

[73] Assignee: Baxter Travenol Laboratories, Inc., Deerfield, Ill.

[21] Appl. No.: 202,390

[22] Filed: Oct. 30, 1980

[51] Int. Cl.[4] ............................................. B01D 31/00
[52] U.S. Cl. .................................... 210/101; 210/103; 210/137; 210/321.2
[58] Field of Search ............ 210/741, 101, 137, 321.1, 210/321.2, 321.3, 103

[56] References Cited

U.S. PATENT DOCUMENTS

| 624,777 | 5/1899 | Fausek | 210/741 |
|---|---|---|---|
| 1,863,103 | 6/1932 | Dowins | 210/137 |
| 2,143,229 | 1/1939 | Aussel | 210/137 |
| 2,454,653 | 11/1948 | Kamp | 210/741 |
| 3,199,677 | 8/1965 | Schneider | 210/137 X |
| 3,976,574 | 8/1976 | White | 210/321.2 |
| 4,197,196 | 4/1980 | Pinkerton | 210/321.3 |

Primary Examiner—John Adee
Attorney, Agent, or Firm—John T. Winburn; Robert A. Benzinger; Paul C. Flattery

[57] ABSTRACT

A transmembrane pressure regulator especially useful in artificial kidney systems. The regulator will maintain a pre-selected dialysate pressure at a substantially constant value despite changes in dialysate flow. The regulator of the invention will adjust dialysate pressure in response to changes in a patient's venous blood pressure so as to maintain a transmembrane pressure substantially constant at a preselected value.

7 Claims, 4 Drawing Figures

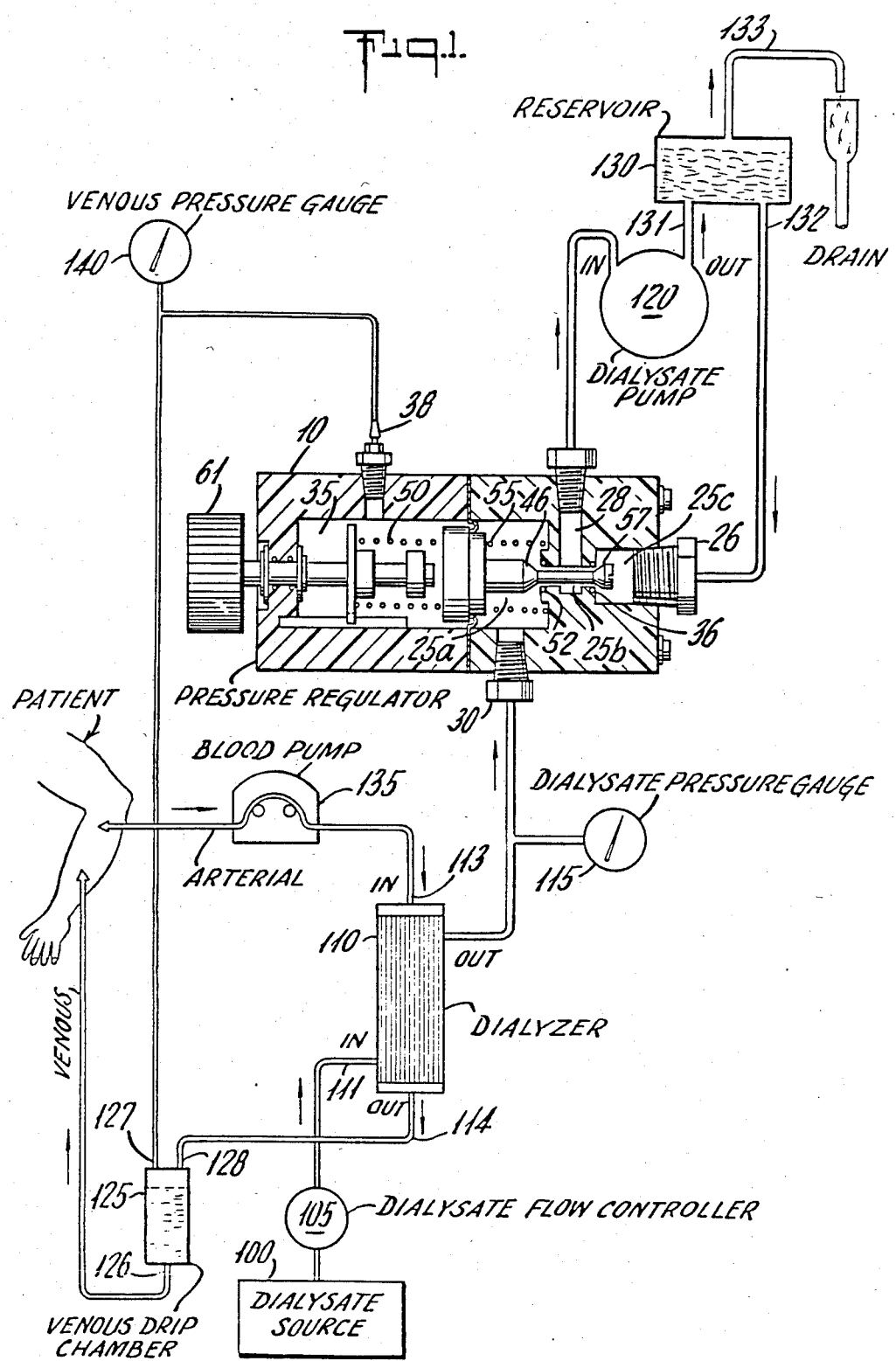

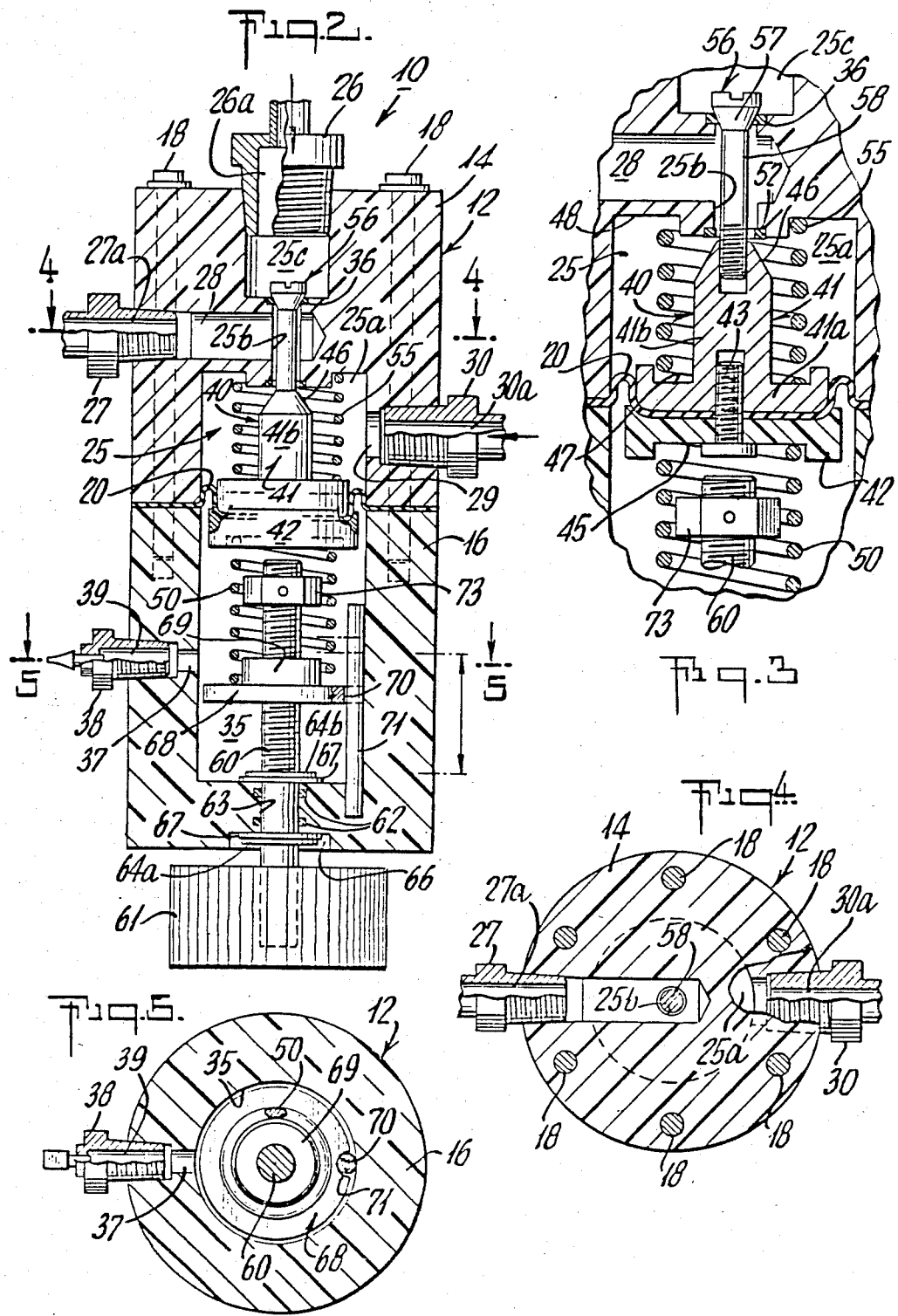

PRESSURE REGULATOR

This invention relates to pressure regulators and particularly to transmembrane pressure regulators for use with blood dialyzers in artificial kidney systems.

DESCRIPTION OF THE PRIOR ART

During kidney dialysis procedures, ultrafiltrate, i.e., water containing dissolved solutes, is removed from the patient's blood through the dialyzer membrane and into the dialysate solution. The rate at which ultrafiltrate is removed depends on the type of dialyzer employed and the pressure differential across the membrane. This pressure differential, referred to as the transmembrane pressure, is the difference between the pressure of the patient's blood on one side of the membrane and the pressure of the dialysate solution flowing through the dialyzer on the opposite side of the membrane. For example, in a typical dialysis procedure, the patient's blood may flow through the dialyzer at a pressure of $+100$ mm. Hg and the dialysate may flow at a pressure of $-100$ mm. Hg, the system thus being characterized by a transmembrane pressure, TMP, of 200 mm. Hg.

Prior to the beginning of a dialysis treatment, the total amount of ultrafiltrate to be removed from the patient is determined and the rate of removal is established. Using data supplied by the dialyzer manufacturer, the transmembrane pressure required to remove the desired amount of ultrafiltrate is determined. If the involved variables, e.g. the patient's blood pressure, the dialysate pressure, etc., remain constant, the desired amount of ultrafiltrate will be removed in the selected time. In actual clinical practice, however, the desired ultrafiltration rate is seldom achieved without constant manual adjustment of the dialysate pressure. Where efforts are made to operate at a selected transmembrane pressure by assuming the existence of a constant venous blood pressure and using a valve to adjust the dialysate pressure, variations in dialysate flow or accumulation of particulate matter in or around the valve seat will cause a change in the dialysate pressure which in turn will cause a change in the selected transmembrane pressure. Variations in dialysate flow and/or accumulation of particulate matter in or around the valve seat can be eliminated by replacing the aforementioned valve with a dialysate pressure regulator. However, even when a dialysate pressure regulator is used, the transmembrane pressure can change due to fluctuations in the patient's venous blood pressure, these fluctuations becoming more significant in cases where the dialysis procedure is being conducted at transmembrane pressure which are low or near zero.

BRIEF SUMMARY OF THE INVENTION

The present invention substantially eliminates the last mentioned problem by providing a transmembrane pressure regulator which will maintain a preset dialysate pressure at a substantially constant value despite changes in dialysate flow or the presence of particulate matter and which will adjust dialysate pressure in response to changes in the patient's venous blood pressure so as to maintain a substantially constant transmembrane pressure.

The transmembrane pressure regulator of the present invention is particularly beneficial when used in the more recently developed dialysis procedures which require operation for an extended period of time at very low transmembrane pressures. Without the benefit of the present transmembrane pressure regulator, a decrease in the patient's venous blood pressure to a level below the dialysate pressure would allow dialysate solution to pass across the dialyzer membrane into the patient's blood supply. Such changes in the venous blood pressure could occur, for example, as a result of a drop in the patient's blood pressure or the presence of an alarm condition under which the blood pump would stop functioning. By using the transmembrane pressure regulator of the present invention, the dialysate pressure will change as the blood pressure changes, thus maintaining a substantially constant pressure drop across the membrane and preventing inadvertent flow of dialysate into the patient's blood.

BRIEF DESCRIPTION OF THE DRAWINGS

The invention will be more clearly understood by reference to the following detailed description and by reference to the appended drawings in which:

FIG. 1 is a block diagram, with parts in section, illustrating a kidney dialysis system employing the transmembrane pressure regulator of the present invention;

FIG. 2 is a vertical cross-section, with some portions broken away, of the transmembrane pressure regulator of the invention;

FIG. 3 is an enlarged view of a portion of FIG. 2;

FIG. 4 is a cross-sectional view, with some portions broken away, taken along line 4—4 of FIG. 2; and FIG. 5 is a cross-sectional view, with some portions broken away, taken along line 5—5 of FIG. 2.

DESCRIPTION OF THE PREFERRED EMBODIMENT

Referring now to FIGS. 2-5 of the drawing, there is shown one embodiment of a regulator in accordance with the present invention. Regulator 10 comprises a generally cylindrical housing 12 consisting of an upper housing portion 14 and a lower housing portion 16. A rolling diaphragm 20 separates the upper housing portion from the lower housing portion, these portions being held together by a plurality of screws 18. The house portions may be made from, for example, an acrylic resin.

Upper housing portion 14 includes a first, interiorly located pressure cavity 25 which is closed by the diaphragm at its lower end and which communicates with the outer top surface of regulator 10 at its upper end. Pressure cavity 25 preferably consists of a lower chamber 25a, an intermediate chamber 25b, and an upper chamber, 25c, all of which are generally cylindrical in shape. As can be seen in FIGS. 2 and 3, lower chamber 25a has a diameter which is somewhat larger than that of upper chamber 25c, while intermediate chamber 25b has a diameter smaller than that of either the upper or lower chamber.

A male inlet 26, which has a continuous internal bore 26a, is threaded into the top of housing 12 so that bore 26a is in fluid communication with upper chamber 25c of pressure cavity 25.

A first passageway 28 is provided in upper housing portion 14 and this passageway leads from intermediate chamber 25b of pressure cavity 25 to the outer surface of the upper housing. A male outlet fitting 27, which has a continuous internal bore 27a, is threaded into passageway 28, thus providing continuous fluid communication between intermediate chamber 25b of pressure cavity 25 and the outside of the housing. A second passageway 29 is provided in upper housing portion 14 and this passageway leads from the lower chamber 25a of pressure cavity 25 to the outside of the housing. A male outlet fitting 30 having a continuous bore 30a is threaded into passageway 29 thus establishing fluid communication from lower chamber 25a of pressure cavity 25 to the outside of the housing. In the preferred embodiment under discussion, inlet 30 and outlet 27 are located on opposite sides of upper housing portion 14. In the position illustrated in FIGS. 2 and 3, lower chamber 25a and intermediate chamber 25b of pressure cavity 25 are in fluid communication with each other. In the position illustrated in FIGS. 2 and 3, upper chamber 25c of pressure cavity 25 is sealed from fluid communication with intermediate chamber 25b by virtue of the fact that the outer surface of the tapered head 57 of screw 56 is seated and sealed against O-ring 36 located in a recess in the bottom of upper chamber 25c. When tapered head 57 is backed away from O-ring 36, there is fluid communication between intermediate chamber 25b and upper chamber 25c.

Lower housing portion 16 comprises second pressure cavity 35 which is closed at its upper end by rolling diaphragm 20. In the preferred embodiment under discussion, pressure cavity 35 is generally cylindrical and has a diameter corresponding to that of lower chamber 25a of first pressure cavity 25. A passageway 37 is provided in lower housing portion 16 and this passageway leads from pressure cavity 35 to the outside of the housing. A male outlet fitting 38 having a continuous bore 39 is threaded into passageway 37, thus establishing fluid communication between pressure cavity 35 and the outside of the housing.

Housing 12 is formed by assembling housing portions 14 and 16 so that lower chamber 25a and the upper part of pressure cavity 35 are facing each other. Lower chamber 25a and the upper part of pressure cavity 35 would be in fluid communication with each other except for the fact that diaphragm 20 is placed between them.

Diaphragm 20 comprises a flexible, substantially fluid impermeable material, such as fabric reinforced silicone rubber or neoprene rubber. A diaphragm of about 0.030 to about 0.050 inches thick has been found suitable. Preferably the diaphragm has an outside diameter substantially equal to the outside diameter of the housing; in any event, its outside diameter must be such as to seal lower chamber 25a from fluid communication with pressure cavity 35.

The diaphragm is mounted in a support 40 consisting of an upper part 41 and a lower part 42. As shown in FIG. 3, the diaphragm is mounted between the two parts which are held together by a screw 43. Lower part 42 of the diaphragm support is generally disc-like in configuration and its upper surface has a recess for receiving diaphragm 20 therein. This recess can have its outer periphery rounded off to avoid inadvertant damage to the diaphragm. The lower surface of the lower part 42 of the diaphragm support has a generally circular recess 45 which, as will be seen hereinafter, is designed to receive the top end of a compressible spring 50. Upper part 41 of the diaphragm support assumes a generally T-shaped configuration, that is, upper part 41 consists of a generally disc-like base portion 41a and an upstanding portion 41b. The upper surface of base portion 41a has a circular recess 47 for receiving one end of a coil spring 55. The other end of the spring 55 is received in a recess 48 at the top of lower chamber 25a of pressure cavity 25. It will be understood that spring 55 is compressed when its ends are received in recesses 47 and 48. A screw 56 having a slotted, tapered head 57 is secured, for example by threads, to upstanding portion 41b. As will be seen in both FIGS. 2 and 3, shaft 58 of screw 56 is disposed within intermediate chamber 25b of pressure cavity 25. The outer surface of tapered head 57 of the screw cooperates with O-ring 36 to form a valve means for regulating the flow of fluid between upper chamber 25c and intermediate chamber 25b. The outer surface of tapered head 57 forms a fluid tight seal when it comes into contact with the aforementioned O-ring 36; when the screw is backed away from O-ring 36, fluid communication is established between chambers 25b and 25c.

Referring now especially to the lower half of FIG. 2 of the drawings, it will be seen that regulator 10 further includes an elongated shaft 60 which is inserted through a hole 63 in the bottom end wall of lower housing portion 16 so as to extend up into pressure cavity 35. That portion of the shaft lying within pressure cavity 35 is threaded. Shaft 60 has a knob 61 secured to that end thereof which projects beyond the bottom end wall of portion 16. A pair of O-rings 62 form a fluid tight seal between the outer surface of shaft 60 and the wall of hole 63.

Shaft 60 is held in place with the use of a pair of metal E-rings 64a and 64b which are sized so as to engage circular grooves cut into the outer periphery of the shaft. E-ring 64a is disposed in an outer recess 66 in the end wall of lower portion 16, while the other E-ring, 64b, is disposed adjacent the bottom of pressure cavity 35. Both E-rings are separated from their adjacent housing surfaces by nylon washers 67.

Within pressure cavity 35 and threaded onto shaft 60, there is a generally circular spring support plate 68 which has a reduced diameter portion 69. Support plate 68, which can be made of any suitable material such as brass or steel, has a cut-out portion 70 at one point on its periphery. This cut-out portion receives a vertically disposed guide pin 71 which is secured, e.g. with the use of any suitable adhesive, in a hole drilled in the interior of the bottom end wall of the device and which extends upwardly into pressure cavity 35. In the embodiment under discussion, guide pin 71 and cut-out portion 70 are circular, and the guide pin extends well over half way into pressure cavity 35. There is a small clearance between guide pin 71 and cut-out portion 70. There is also a small clearance between the outermost periphery of support plate 68 and the wall of pressure cavity 35. A collar 73 with a set screw, or similar retaining means, is placed on shaft 60 above support plate 68 to limit the distance which support plate 68 can travel upwardly along shaft 60. In the preferred embodiment, shaft 60, base 68, guide pin 71 and retaining means 73 are made of metal.

One end of coil spring 50 is disposed over reduced portion 69 and rests against the enlarged diameter portion of support plate 68. The other end of spring 50 is disposed within recess 45 in the lower surface of lower part 42 of the diaphragm support. This arrangement keeps the spring in its proper position and prevents undesirable sideways slippage.

As can be seen in FIG. 2 and 3, the upstanding portion 41b of the diaphragm support has a tapered end portion 46. An O-ring 52 is placed in a recess in the upper end wall of chamber 25a. There is a clearance between the interior surfaces of O-ring 52 and the outer surface of shaft 58. The outer surface of tapered end portion 46 cooperates with O-ring 52 to form a valve means for regulating the flow of fluid between lower chamber 25a and intermediate chamber 25b. It will be understood that the diaphragm support can be moved upwardly, that is, toward the top of the drawing as the reader views FIG. 2, by using knob 61 to turn shaft 60. When this is done, spring support plate 68 moves upwardly, thereby compressing spring 50 which in turn forces the diaphragm support upwardly. If the shaft has been rotated sufficiently, tapered end portion 46 seats and seals against O-ring 52 placed in the circular recess in the top wall of lower portion 25a of pressure cavity 25.

When tapered portion 46 is sealed against O-ring 52, a fluid tight seal is formed which prevents fluid communication between lower portion 25a and intermediate portion 25b of pressure cavity 25. At the same time, tapered portion 57 of screw 56 is unseated from O-ring 36, thus establishing fluid communication between intermediate chamber 25b and upper chamber 25c of pressure cavity 25. When tapered portion 46 is backed away from O-ring 52, fluid communication is established between lower chamber 25c and intermediate chamber 25b. It should be noted that tapered portion 57 and tapered portion 46 can simultaneously assume intermediate positions in which neither tapered portion 57 nor tapered portion 46 are sealed against their respective O-rings 36 and 52. This intermediate positioning can be seen in FIG. 1. In such intermediate positions, there is fluid communication between and among lower, intermediate, and upper chambers 25a, 25b, and 25c of pressure cavity 25. The degree of fluid communication, of course, is more or less restricted depending on the degree to which the sealing surfaces of tapered portions 57 and 46 are backed away from the sealing surfaces of O-rings 36 and 52, respectively. The tapered portion 57 of screw 56 and O-ring 36 comprise valve means for regulating fluid flowing from inlet 26 through pressure cavity 25 into passageway 28. Tapered portion 46 and O-ring 52 comprise another valve means for regulating fluid flow from inlet 30 through pressure cavity 25 into passageway 28.

Spring 55 is compressed when it is in its position within lower chamber 25a of pressure cavity 25. Thus, spring 55 always exerts a downward force against diaphragm support 40, thus bringing, or tending to bring, tapered portion 57 of screw 56 into sealing contact with O-ring 36. Spring 50 has a slight degree of compression when it is in its position within pressure cavity 35 and when spring support plate 68 is in its lowermost position on shaft 60. The degree of compression of spring 50 may be increased by turning knob 61 so as to raise spring support plate 68 upwardly along shaft 60. When spring 50 has insufficient compression to overcome the compression of spring 55, tapered portion 57 is seated against O-ring 36. By raising spring support plate 68 upwardly on shaft 60, the compression on spring 50 can be increased to such a degree that tapered portion 57 is not seated against O-ring 36 nor is tapered portion 46 seated against O-ring 52. When the compression of spring 50 is even further increased, the downward force exerted by spring 55 is overcome and tapered portion 46 is brought into sealing contact with O-ring 52. It should be noted that the comments of this paragraph apply to regulator 10 when it is not connected to a kidney dialysis system. Other factors, specifically those forces exerted by the fluids in pressure cavities 25 and 35 must be considered when regulator 10 is functioning as a component of a kidney dialysis system.

It is preferable during the final assembly of pressure regulator 10 to fill pressure cavity 35 with a substantially non-compressible fluid. This fluid must not deleteriously affect the other parts of the regulator with which it comes into contact. White oil NF has been found suitable for this purpose, but other non-compressible fluids such as water and silicone-based oils may also be used. Where the non-compressible fluid is used, outlet 38 should be temporarily plugged so as to prevent leakage during shipping and storage and the regulator is used with outlet 38 oriented in the upward direction as illustrated in FIG. 1. It will be recognized that pressure regulator 10 will function properly even without cavity 35 being filled with a non-compressible fluid. In such a case, however, there may be substantial changes in the blood level in the venous blood drip chamber if the patient's venous blood pressure changes to any substantial degree. If the patient's venous blood pressure increases sufficiently, blood could overflow the drip chamber and wet out the liquid barrier customarily used in the line between the drip chamber and the venous blood pressure gauge. If the patient's venous blood pressure decreases sufficiently, the level of blood in the drip chamber may drop, thus raising the possibility of entraining air in the blood being returned to the patient. When pressure cavity 35 is filled with a substantially non-compressible fluid, changes in the patient's venous blood pressure will result in only minor changes in the blood level in the drip chamber.

The use of the regulator of the present invention will now be described in conjunction with the operation of a kidney dialyzer. In particular, the use of the regulator will be described in conjunction with an extracorporeal dialysis system comprising, in addition to the regulator, a blood dialyzer, a venous blood drip chamber, a venous pressure gauge, a source of dialysate, a dialysate flow controller, a dialysate pressure gauge, and a dialysate reservoir.

Referring now to FIG. 1, there is shown an extracorporeal dialysis system comprising a source 100 of dialysate, a dialysate flow controller 105, a hollow fiber blood dialyzer 110, a dialysate pressure gauge 115, regulator 10, a dialysate pump 120, a venous blood drip chamber 125, a reservoir 130, a blood pump 135, and a venous blood pressure gauge 140.

In the system of FIG. 1, dialysate flows at positive pressure from dialysate source 100 into flow controller 105 which, in a typical dialysis procedure, may be operating at an output of 500 cc/min. The dialysate leaves the flow controller and enters the dialysate inlet 111 on dialyzer 110. After flowing through the dialyzer, the dialysate exits through the dialysate outlet 112 and flows through tubing connected to inlet 30 of regulator 10 and into lower portion 25a of pressure cavity 25.

Dialysate pressure gauge 115, which is located between the dialysate outlet of the dialyzer and inlet 30 of regulator 10, measures the pressure of the dialysate which, typically, might range from +50 mm Hg to −450 mm Hg.

Outlet 27 on regulator 10 is connected by tubing to the inlet side of dialysate pump 120. Tubing connected to the outlet side of the dialysate pump leads to the inlet 131 of reservoir 130. The dialysate pump in a typical dialysis procedure operates at a flow rate of 1100 cc/minute. Reservoir 120 also comprises an outlet 133 for air and spent dialysate, this outlet being connected by tubing to a floor drain. The rate of flow of dialysate to drain corresponds to the rate of flow of dialysate at the output side of controller 105. Reservoir 130 also has a return outlet 132 at its bottom, this outlet being connected by tubing to inlet 26 of regulator 10.

During the dialysis procedure, blood to be treated is withdrawn from a patient and pumped by blood pump 135, which typically operates at 200 cc./minute, through tubing to the blood inlet 113 of the dialyzer. After passing through and exiting the dialyzer at blood outlet 114, the dialyzed blood flows through tubing into the inlet 128 of venous blood drip chamber 125. The blood then flows through the blood outlet 126 of the drip chamber and is returned to the patient through tubing connected to a vein of the patient. At the top of the blood drip chamber there is a pressure measurement outlet 127 which is connected by tubing to inlet 38 of regulator 10. Venous blood pressure gauge 140 is connected to the tubing at a point between pressure measurement outlet 127 and inlet 38 of the regulator. A barrier, impermeable to liquids such as blood but permeable to a gas such as air, is placed in the line between gauge 140 and pressure measurement outlet 127 of the regulator.

In order to facilitate understanding how regulator 10 works, it will be assumed in the discussion which follows that the ultrafiltration (UF) coefficient of dialyzer 110 is 3.0 cc. of ultrafiltrate/hr./mm. Hg; that blood pump 135 is operating at an output of 200 cc./minute; that dialysate leaves flow controller 105 at the rate of 500 cc./minute, and that dialysate pump 120, which is a positive displacement pump, is operating at a flow rate of 1100 cc./minute. It will be further assumed that it is desired to remove from the patient 600 cc. of ultrafiltrate per hour.

$$\text{Since } TMP = \frac{\text{Ultrafiltration Rate}}{\text{Ultrafiltration Coefficient}} = \frac{600 \text{ cc/hr.}}{3 \text{ cc/hr./mm.hg.}}$$

it will be necessary to operate the system at a TMP of 200 mm. Hg.

As used herein, the term transmembrane pressure, or TMP, is the difference between the venous blood pressure measured at the dialyzer blood outlet by venous blood pressure gauge 140 and the dialysate pressure measured at the dialysate outlet of the dialyzer by dialysate pressure gauge 115.

With the system set up as illustrated in FIG. 1, blood pump 135 is activated, after which the venous blood pressure is read on gauge 140. Knob 61 on regulator 10 is then adjusted so as to obtain that dialysate pressure which is needed to produce a TMP of 200 mm. Hg. If, for example, it is found, after the blood pump is activated, that the venous pressure is +100 mm. Hg., it will be necessary to adjust regulator 10 by turning knob 61 until the dialysate pressure gauge indicates a dialysate pressure of −100 mm. Hg. This will establish a transmembrane pressure of 200 mm. Hg., that is, the difference between the venous blood pressure, +100 mm. Hg. and the dialysate pressure, −100 mm. Hg., will be 200 mm. Hg. Assuming for the moment that there is no change in the variables affecting the system, the TMP will remain at 200 mm. Hg. and the valve means in the regulator will assume intermediate positions illustrated generally in FIG. 1. In other words, as long as the system remains undisturbed, there will be a clearance between O-ring 36 and the tapered outer surface 57 of screw 56 and there will be a clearance between O-ring 52 and the tapered outer surface 46 of the upper part 41 of the diaphragm support.

It will be understood that, when knob 61 of regulator 10 was adjusted to give the desired dialysate pressure of −100 mm. Hg., a certain degree of compression was imparted to spring 50. This compression of spring 50, in turn, acts on and tends to compress spring 55. As the compression of spring 50 is increased, this spring acts with increasing force against the bottom of the diaphragm support, thus effectively reducing the force with which spring 55 acts, in the opposite direction, against the top of the diaphragm support.

Each spring exerts a certain force which is characteristic of the specific degree of compression which it has assumed. Once the desired TMP has been established, it will not be necessary to make any further adjustments of knob 61 of the regulator (unless, of course, it is desired to actually change the TMP). As long as the adjustment on regulator 10 remains unchanged, the force, $F_{55}$, exerted by spring 55 will not change, nor will there be a change in the force, $F_{50}$, exerted by spring 50. It therefore follows that the quantity $(F_{50}-F_{55})$ will remain unchanged.

By referring again to FIG. 3, it will be seen that the force, $F_{35}$, acting in pressure cavity 35 against diaphragm 20 will be the sum of the force, $F_{50}$, exerted by spring 50 in its compressed state and the force, $P_{35}$, generated by the pressure of the fluid in cavity 35 acting on the effective area, $A_D$, of the diaphragm.

In other words, $$F_{35} = F_{50} + (P_{35} \times A_D).$$

Similarly, the force, $F_{25a}$, acting in lower chamber 25a of pressure cavity 25 against diaphragm 20 will be the sum of the force, $F_{55}$, exerted by spring 55 in its compressed state and the force, $P_{25a}$, generated by the pressure of the dialysate in chamber 25a acting on the effective area, $A_D$, of the diaphragm.

In other words, $$F_{25a} = F_{55} + (P_{25a} \times A_D).$$

Since at equilibrium, $F_{35} = F_{25a}$, it follows that $$F_{50} + (P_{35} \times A_D) = F_{55} + (P_{25a} \times A_D) \quad [\text{Eq. 1}]$$

Rearranging Equation 1, it will be seen that $$(F_{50} - F_{55}) = A_D(P_{25a} - P_{35}) \quad [\text{Eq. 2}]$$

As explained earlier, the value $(F_{50}-F_{55})$ will be a constant for any particular setting of knob 61. As can be seen from Equation 2, a change in the venous pressure, $P_{35}$, in pressure cavity 35 will produce a corresponding change in the dialysate pressure in lower pressure chamber 25a. Thus the transmembrane pressure, $P_{25a}-P_{35}$, will remain constant at the desired value.

To understand how regulator 10 functions to maintain a constant transmembrane pressure, let it now be assumed that the venous blood pressure increases from the aforementioned value of +100 mm. Hg. to a new value of +150 mm. Hg. As required by Equation 2, the dialysate pressure will change from −100 mm. Hg. to −50 mm. Hg., that is, regulator 10 will function so as to increase the dialysate pressure, thus maintaining the transmembrane pressure at the desired value of 200 mm.

Hg. When the venous blood pressure increases, the pressure of the fluid in pressure cavity 35 increases, and the forces acting against the bottom of the diaphragm support are increased. These increased forces move the tapered portion 57 of screw 56 a slight distance further away from O-ring 36, that is, the clearance between the tapered portion and the O-ring is increased. This increased clearance allows an increased amount of dialysate to flow from reservoir 130 through upper chamber 25c of pressure cavity 25 and into intermediate chamber 25b. This increased amount of dialysate, along with the amount of dialysate reaching lower chamber 25a from the dialysate outlet of the dialyzer, is now available to pass through passageway 28 to satisfy the demand of the dialysate pump. Since the amount of dialysate now being supplied to the dialysate pump has been increased, the pressure of the dialysate as measured by the dialysate pressure gauge is increased, that is, the dialysate pressure has changed from a higher negative value, i.e. −100 mm. Hg., to a lower negative value, i.e. −50 mm. Hg. The amount of the increase in the dialysate pressure is 50 mm. Hg. which corresponds to the increase in the venous blood pressure. Since the dialysate pressure and the venous blood pressure have increased by identical amounts, the difference between the two values, that is, the transmembrane pressure, remains constant.

It will be recognized that the foregoing discussion applies to the operation of a dialysis system in which the dialysate pressure has a negative value. The negative pressure on the dialysate was in general produced by the suction action of the positive displacement type dialysate pump 120. In particular, as has been discussed above, the exact amount of negative dialysate pressure was produced and maintained at the desired value by varying the clearance between tapered portion 57 of screw 56 and O-ring 36. The regulator of the invention can also be used to operate a dialysis system in which the dialysate pressure is controlled at a positive value, that is, at a value above atmospheric pressure. For example, let it be assumed again that the venous blood pressure measured by the venous blood pressure gauge is +100 mm. Hg. and that it is desired to operate at a TMP of 75 mm. Hg. It will thus be necessary to establish a dialysate pressure of +25 mm. Hg. Knob 61 is turned until the dialysate pressure gauge reads +25 mm. Hg. The desire TMP of 100 mm. Hg. has now been established and the tapered portion 46 of the upper part of the diaphragm support has approached, but has not seated against, O-ring 52. At the same time, tapered portion 57 of screw 56 has been backed away from O-ring 36, thereby allowing dialysate to recirculate freely from reservoir 130, through upper chamber 25c, into intermediate chamber 25b, through passageway 28 to the inlet of the dialysate pump and finally back to reservoir 130. Due to the reduced clearance between tapered portion 46 and O-ring 52, pressure begins to build up in lower chamber 25a and in those portions of the circuit upstream thereof, because the dialysate flow controller 105 continues to supply dialysate at 500 cc./minute. This increased pressure acts against the effective area of diaphragm 20 in chamber 25a and moves tapered portion 46 away from O-ring 52 a sufficient distance to establish pressure equilibrium and to satisfy the conditions of Equation 2.

The desired transmembrane pressure of 75 mm. Hg. will now be maintained constant despite changes in venous pressure. For example, if the venous pressure changes from +100 mm. Hg. to +125 mm. Hg., there will be a corresponding change in dialysate pressure from +25 mm. Hg. to +50 mm. Hg., thus maintaining the desired TMP of 75 mm. Hg. This happens as follows. When the venous pressure increases, this pressure increase is transmitted to the fluid in pressure cavity 35. This increases the forces acting against the effective area of diaphragm 20 in pressure cavity 35 and pushes tapered portion 46 toward O-ring 52, thus producing an increase in the dialysate pressure in lower chamber 25a of pressure cavity 25. The amount of the increase in the dialysate pressure corresponds to the increase in venous blood pressure, that is, the dialysate pressure increases from +25 mm. Hg. to +50 mm. Hg. Since the dialysate pressure and venous blood pressure have increased by the same amounts, the difference between these two valves, that is, the transmembrane pressure, remain constant at the selected value.

It will be recognized that variations can be made in the structure of regulator 10 without departing from the spirit and scope of the invention. Other types of valving may be used instead of the tapered surface/O-ring combinations disclosed earlier herein. One or both of the springs employed in the regulator for biasing the diaphragm could be replaced by equivalent structures performing the same functions; a compressible piece of silicone rubber, for example, might be used. Threaded shaft 60 could be replaced with a rotatable cam means in which the cam lob would bear against support plate 68 to compress spring 50.

Although the use of regulator 10 has been described in conjunction with a dialysis system employing a blood dialyzer of the hollow fiber type, it will be understood that the regulator will also work in dialysis systems containing other types of blood dialyzers in which dialysate pressure can be varied in order to control the amount of ultrafiltration.

We claim:

1. A transmembrane pressure regulator comprising an upper housing portion and a lower housing portion separated from each other by a rolling diaphragm, said upper housing portion having a first interiorly located cavity connected by first, second, and third separate passageways to the outside of said regulator, said lower housing portion having a second interiorly located cavity connected by a fourth separate passageway to the outside of said regulator, said diaphragm being secured to said regulator so as to separate said housing portions and to prevent fluid communication between the respective cavities of said housing portions, means associated with said upper housing portion for biasing said diaphragm in the direction of said lower housing portion, first means associated with said upper housing for regulating the amount of fluid flowing from said first passageway through said first cavity and into said second passageway, second means associated with said upper housing for regulating the amount of liquid flowing from said third passageway through said first cavity and into said second passageway, and means associated with said lower housing portion for adjustably biasing said diaphragm in the direction of said upper housing portion.

2. A transmembrane pressure regulator according to claim 1 wherein the cavity in the lower housing portion contains a substantially non-compressible fluid.

3. A transmembrane pressure regulator comprising an upper housing portion and a lower housing portion separated from each other by a rolling diaphragm, said upper housing portion having an interiorly located cavity which includes an upper chamber, an intermediate chamber, and a lower chamber, each of said chambers being connected by a separate passageway to the outside of said regulator, said lower chamber being in fluid communication with said intermediate chamber and said intermediate chamber being in fluid communication with said upper chamber, said diaphragm being secured in a diaphragm support comprising a lower part and an upper part, the upper part of said diaphragm support including first and second tapered portions located at opposite ends of a shaft portion, said first tapered portion being adapted to cooperate with a first sealing means in the bottom of said upper chamber so as to form therewith a valve means for controlling flow of fluid between said upper chamber and said intermediate chamber, said second tapered portion being adapted to cooperate with a second sealing means in the top of said lower chamber so as to form therewith a valve means for controlling the amount of a fluid flowing between said intermediate chamber and said lower chamber, means in said upper chamber for biasing said diaphragm in the direction toward said lower housing portion, said lower housing portion having an interiorly located cavity connected by a passageway to the outside of said regulator, said cavity in said lower housing portion having located therein means for adjustably biasing said diaphragm in the direction of said upper housing portion.

4. A transmembrane pressure regulator according to claim 3 wherein the cavity in said lower housing portion contains a substantially non-compressible fluid.

5. A transmembrane pressure regulator according to claim 4 wherein said non-compressible fluid is selected from the group consisting of mineral oil, water, and silicone-based oils.

6. A transmembrane pressure regulator according to claim 3 wherein the means in said lower housing portion for adjustably biasing the diaphragm in the direction of the upper housing include a spring, a threaded shaft, and a follower plate located within said lower housing portion, said follower plate being threaded onto said threaded shaft and said spring being positioned between said follower plate and the upper end wall of the lower housing portion.

7. A transmembrane pressure regulator according to claim 6 wherein said shaft extends in fluid tight relationship through the bottom wall of the lower housing portion.

* * * * *